(12) United States Patent
Lai et al.

(10) Patent No.: US 9,821,002 B2
(45) Date of Patent: Nov. 21, 2017

(54) METHOD FOR ALLEVIATING RADIATION INJURY WITH ISORHAMNETIN-3-O-β-D-GLUCOSIDE

(71) Applicant: Sinotai Oncology Associate., Ltd., Taichung (TW)

(72) Inventors: Icheng Lai, Taichung (TW); Alicia Lai, Taichung (TW)

(73) Assignee: Sinotai Oncology Associate., LTD., Taichung (TW)

( * ) Notice: Subject to any disclaimer, the term of this patent is extended or adjusted under 35 U.S.C. 154(b) by 167 days.

(21) Appl. No.: 14/982,141

(22) Filed: Dec. 29, 2015

(65) Prior Publication Data

US 2017/0007632 A1 Jan. 12, 2017

(30) Foreign Application Priority Data

Jul. 7, 2015 (TW) .............................. 104122017 A

(51) Int. Cl.
*A61K 31/7048* (2006.01)
*A61Q 19/00* (2006.01)

(52) U.S. Cl.
CPC .......... *A61K 31/7048* (2013.01); *A61Q 19/00* (2013.01); *A61K 2800/10* (2013.01); *A61K 2800/74* (2013.01)

(58) Field of Classification Search
None
See application file for complete search history.

(56) References Cited

U.S. PATENT DOCUMENTS

2002/0151599 A1* 10/2002 Buchholz ............... A61K 8/498
514/685

* cited by examiner

*Primary Examiner* — Traviss C McIntosh, III
(74) *Attorney, Agent, or Firm* — Cesari and McKenna LLP

(57) ABSTRACT

Disclosed herein is a method for alleviating radiation injury, which includes administering to a subject in need thereof a composition containing isorhamnetin-3-O-β-D-glucoside.

13 Claims, 4 Drawing Sheets

METHOD FOR ALLEVIATING RADIATION INJURY WITH ISORHAMNETIN-3-O-β-D-GLUCOSIDE

CROSS-REFERENCE TO RELATED APPLICATIONS

This application claims priority of Taiwanese Application No. 104122017, filed on Jul. 7, 2015.

BACKGROUND

Technical Field

The present disclosure relates to a method for alleviating radiation injury with a composition containing isorhamnetin-3-O-β-D-glucoside.

Background Information

Radiation is the emission or transmission of energy in the form of waves or particles through space or a material medium. In general, radiation is classified as: (1) ionizing radiation, which refers to high-energy electromagnetic waves (e.g., X-rays and gamma rays) or particles (e.g., alpha particles, beta particles and neutrons) capable of ionizing atoms or molecules; and (2) non-ionizing radiation, which refers to low-energy electromagnetic waves (e.g., visible light, infrared, ultraviolet and microwaves) not capable of ionizing atoms or molecules. Radiation exposure to organisms can lead to DNA damage, thereby causing gene mutation and inducing apoptosis and cell death, and finally resulting in radiation injury (including ionizing radiation injury and non-ionizing radiation injury).

Ionizing radiation injury may be classified into the following three categories based on the degree of radiation exposure:

(1) acute radiation syndrome (ARS), also known as radiation poisoning and radiation sickness, which is caused when the entire human body is exposed to ionizing radiation over a short period of time (e.g., within 24 hours), and whose symptoms may be classified as related to the hematopoietic system (e.g., aplastic anemia), gastrointestinal system (e.g., nausea and vomiting) and neurovascular system (e.g., dizziness);
(2) chronic radiation syndrome (CRS), which is caused when the entire human body is exposed to ionizing radiation over a long period of time (e.g., several months or years), and whose symptoms include skin atrophy, cataracts, sterility, etc.; and
(3) injury caused by radiation therapy, which results when a specific part of a human subject is exposed to ionizing radiation, and whose symptoms include anorexia, lassitude, diarrhea, erythema, desquamation, bowel stenosis, necrosis of bone, fibrosis of lung, etc.

The radioprotective agents used clinically to alleviate radiation injury include: free radical scavengers (e.g., catalase), antioxidants (e.g., vitamin E), cytokines (e.g., interleukin-1), thiols (e.g., Amifostine) and steroids (e.g., 5-Androstenediol). Among these, Amifostine is the only radioprotective agent approved by the Food and Drug Administration (FDA). Although Amifostine is effective in protecting tissues against radiation injury, it also leads to severe side effects (e.g., nausea, vomiting and hypotension) in users. Therefore, researchers in this field have attempted to find active components within traditional Chinese medicine that can be used to treat and/or prevent radiation injury.

*Hippophae rhamnoides* L. (trivial name: sea-buckthorn; SHA JI in pinyin) is a deciduous shrub which belongs to the genus *Hippophae* and family Elaeagnaceae. *Hippophae rhamnoides* L. can be found in the Chinese provinces: Hebei, Shanxi, Shaanxi, Gansu, Qinghai, etc. Studies have indicated that *Hippophae rhamnoides* L. can be used to treat liver injuries, gastric ulcers, tumors, etc. (Cheng T. J. (1992), *Zhonghua Yu Fang Yi Xue Za Zhi*, 26:227-229; Xing J. et al. (2002), *Fitoterapia*, 73:644-650; Yasukawa K. et al. (2009), *Fitoterapia*, 80:164-167).

Research regarding radioprotection of *Hippophae rhamnoides* L. extracts has begun to attract attention in recent years. For example, in Chawla R. et al. (2007), *J. Med. Food*, 10:101-109, the dried and powdered berries of *Hippophae rhamnoides* L. were extracted with ethanol, followed by filtration and concentration. The viscous extract thus obtained was washed with hot hexane and ether to remove nonpolar fractions. The remaining extract was passed over a bed of silica gel using a mixture of ethyl acetate and methanol [40:60 (v/v)] as an eluent. The partially purified fractions were again passed through a column containing a weakly polar polymeric adsorbent resin, followed by elution using 20-80% ethanol in water so as to obtain fractionated extracts. The fractionated extracts were pooled and concentrated to obtain a flavonoid-rich fraction, and designated REC-1001. High performance liquid chromatography (HPLC) revealed the presence of kaempferol, isorhamnetin and quercetin in REC-1001. REC-1001 was further subjected to bioactivity analysis, and results proved that REC-1001 possesses antioxidant, free radical scavenging and radioprotective activities. Therefore, Chawla R. et al. deem that kaempferol, isorhamnetin and quercetin in REC-1001 confer REC-1001 with the above-mentioned bioactivities, and REC-1001 may be a safe and effective antioxidant nutraceutical product.

Isorhamnetin is a flavonoid present in medicinal plants (e.g., *Persicaria thunbergii*, *Hippophae rhamnoides* L. and *Brassica campestris* L.), and has the following formula (I):

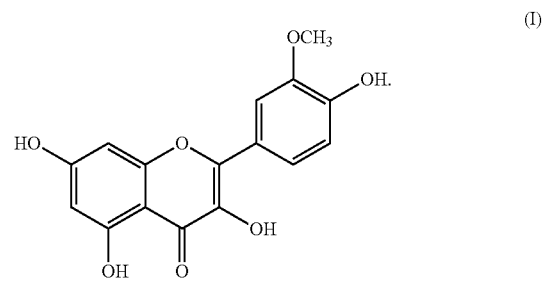 [SMILES: COc1cc(-c2oc3cc(O)cc(O)c3c(=O)c2O)ccc1O]

It is known that isorhamnetin is effective in preventing endothelial cell injury, treating enteritis, and possesses anti-tumor and anti-adipogenesis properties (Bao M. and Lou Y. (2006), *Eur. J. Pharmacol.*, 547:22-30; Teng B. S. et al. (2006), *Pharmacol. Res.*, 54:186-194; Lee J. et al. (2010), *Life Sci.*, 86:416-423; CN 103462957 A).

Isorhamnetin glycosides are derivatives of isorhamnetin. Common isorhamnetin glycosides include isorhamnetin-3-O-β-D-glucoside, isorhamnetin-3-O-β-D-rutinoside, isorhamnetin-3-O-galactoside, etc. Isorhamnetin-3-O-β-D-glucoside can be isolated from *Hippophae rhamnoides* L., *Cochlospermum religiosum* and *Brassica campestris* L. Isorhamnetin-3-O-β-D-glucoside is a flavonoidal glucoside, and it has the following formula (II):

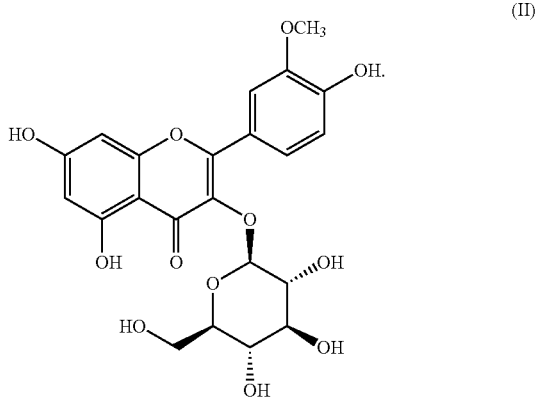 [SMILES: COc1cc(-c2oc3cc(O)cc(O)c3c(=O)c2O[C@@H]2O[C@H](CO)[C@@H](O)[C@H](O)[C@H]2O)ccc1O]

(II)

Studies have indicated that isorhamnetin-3-O-β-D-glucoside is effective in treating tumor and diabetes, preventing liver injury and retarding selenite-induced cataract (CN 1518986 A; Lee Y. S. et al. (2005), Biol. Pharm Bull., 28:916-918; Igarashi K. et al. (2008), Biosci. Biotechnol. Biochem., 72:856-860; Devi V. G. et al. (2010), Toxicol In Vitro., 24:1662-1669).

As far as the inventors are aware, there have been no documents or prior art patents which disclose that isorhamnetin-3-O-β-D-glucoside can be utilized in the alleviation of radiation injury.

SUMMARY

Therefore, the present disclosure provides a method for alleviating radiation injury, comprising administering to a subject in need thereof a composition containing isorhamnetin-3-O-β-D-glucoside.

BRIEF DESCRIPTION OF THE DRAWINGS

Other features and advantages of the present disclosure will become apparent in the following detailed description of the embodiments with reference to the accompanying drawings, of which.

DETAILED DESCRIPTION

Figure 1:
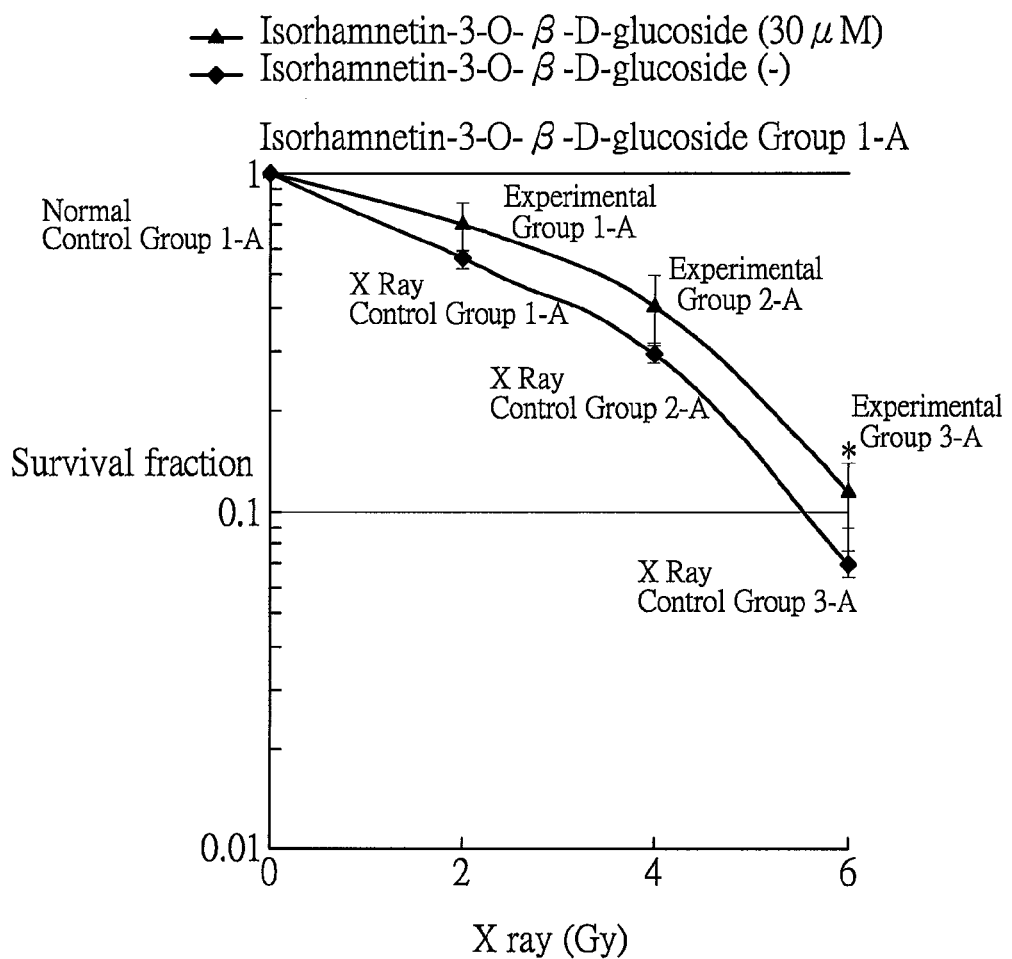
FIG. 1 shows the survival fraction of BNL CL.2 cells in each group as determined via clonogenic assay, in which the symbol "*" represents p<0.05 when compared with X-Ray Control Group 3-A.

It is to be understood that, if any prior art publication is referred to herein, such reference does not constitute an admission that the publication forms a part of the common general knowledge in the art, in Taiwan or any other country.

For the purpose of this specification, it will be clearly understood that the word "comprising" means "including but not limited to", and that the word "comprises" has a corresponding meaning.

Unless defined otherwise, all technical and scientific terms used herein have the meaning commonly understood by a person skilled in the art to which the present disclosure belongs. One skilled in the art will recognize many methods and materials similar or equivalent to those described herein, which could be used in the practice of the present disclosure. Indeed, the present disclosure is in no way limited to the methods and materials described.

According to the present disclosure, isorhamnetin-3-O-β-D-glucoside has been proven to be able to effectively protect cells (including mouse liver cells, mouse mammary gland epithelial cells and human skin keratinocytes) against X-ray-induced death, X-ray-induced cell death, X-ray-induced apoptosis and ultraviolet-induced apoptosis.

Accordingly, the present disclosure provides a method for alleviating radiation injury, comprising administering to a subject in need thereof a composition containing isorhamnetin-3-O-β-D-glucoside.

As used herein, the term "alleviating" or "alleviation" refers to reducing, ameliorating, relieving, or controlling one or more clinical signs of a disease or disorder, and lowering, stopping, or reversing the progression of severity regarding the condition or symptom being treated.

As used herein, the term "radiation injury" refers to an injury or damage that is caused by exposure of any portion of an organism to radiation.

According to the present disclosure, the radiation injury is an ionizing radiation injury.

According to the present disclosure, the ionizing radiation injury includes one of an acute radiation syndrome (ARS), a chronic radiation syndrome (CRS), or injury caused by radiation therapy.

As used herein, the term "acute radiation syndrome" (ARS) refers to acute symptoms caused by exposure of the entire body of an organism to the ionizing radiation over a short period of time (e.g., within 24 hours). The acute symptoms include, but are not limited to, symptoms related to the hematopoietic system (e.g., aplastic anemia, hemolysis and atrophy of lymph nodes), symptoms related to the gastrointestinal system (e.g., nausea, vomiting and abdominal pain), and symptoms related to the neurovascular system (e.g., dizziness, headache and decreased level of consciousness).

As used herein, the term "chronic radiation syndrome" (CRS) refers to chronic symptoms caused by exposure of the entire body of an organism to the ionizing radiation over a long period of time (e.g., several months or years). The chronic symptoms include, but are not limited to, skin atrophy, cataract, recurrent infection, low grade fever, loss of appetite, fatigue, fainting and hair loss.

As used herein, the term "injury caused by radiation therapy" refers to symptoms caused by exposure of a specific portion of a human subject to the ionizing radiation. The symptoms include, but are not limited to, anorexia, lassitude, diarrhea, erythema, desquamation, bowel stenosis, necrosis of bone and fibrosis of lung.

According to the present disclosure, the radiation injury is a non-ionizing radiation injury. In an embodiment of the present disclosure, the non-ionizing radiation injury is ultraviolet damage.

As used herein, the term "ultraviolet damage" refers to symptoms caused by ultraviolet overexposure of any portion of a human subject. The symptoms include, but are not limited to, skin inflammation, delayed tanning reaction, severe pains in the joints and muscles and around the eyes, shock, fever, nausea, vomiting and generalized weakness.

According to the present disclosure, isorhamnetin-3-O-β-D-glucoside can be prepared by synthetic techniques well known to chemists.

Alternatively, isorhamnetin-3-O-β-D-glucoside can be isolated and purified from natural sources by isolation and purification methods commonly used in the art. In this aspect, reference is made to, e.g., Lee Y. S. et al. (2005), supra, and Igarashi K. et al. (2008), supra.

According to the present disclosure, the natural sources include one of *Brassica campestris* L., *Callianthemum taipaicum*, *Foeniculum vulgare* Mill., *Hippophae rhamnoides* L., *Inula britannica*, *Sedum formosanum*, *Brassica juncea*, *Caragana arborescens* Lam., *Opuntia dillenii* (Ker-Gawl) Haw. and *Salicornia herbacea*.

According to the present disclosure, the composition containing isorhamnetin-3-O-β-D-glucoside may be a pharmaceutical composition that could be formulated into a suitable dosage form for parenteral, oral or topical administration using technology well known to those skilled in the art. The suitable dosage form includes, but is not limited to, injections (e.g. sterile aqueous solutions or dispersions), sterile powder, tablets, troches, lozenges, capsules, dispersible powder or granules, solutions, suspensions, emulsions, syrups, elixirs, slurries, external preparations, and the like.

The pharmaceutical composition according to the present disclosure may further include a pharmaceutically acceptable carrier widely employed in the art of drug-manufacturing. For instance, the pharmaceutically acceptable carrier may include one or more of the following agents: solvents, buffers, suspending agents, decomposers, disintegrating agents, dispersing agents, binding agents, excipients, stabilizing agents, chelating agents, diluents, gelling agents, preservatives, lubricants, absorption delaying agents, liposomes, and the like. The choice and amount of the aforesaid agents are within the expertise and routine skills of those skilled in the art.

The pharmaceutical composition according to the present disclosure may be administered via one of the following parenteral routes: intraperitoneal injection, subcutaneous injection, intramuscular injection, and intravenous injection.

In an embodiment of the present disclosure, the pharmaceutical composition is formulated into a suitable dosage form for subcutaneous injection.

The pharmaceutical composition according to the present disclosure can be formulated into an external preparation suitable for topical application to the skin using technology well known to those skilled in the art. The external preparation includes, but is not limited to, emulsions, gels, ointments, creams, patches, liniments, powder, aerosols, sprays, lotions, serums, pastes, foams, drops, suspensions, salves, and bandages.

According to the present disclosure, the external preparation is prepared by admixing the pharmaceutical composition with a base that is well known and commonly used in the art.

According to the present disclosure, the base may include one or more of the following additives: water, alcohols, glycol, hydrocarbons (such as petroleum jelly and white petrolatum), waxes (such as paraffin and yellow wax), preserving agents, antioxidants, surfactants, absorption enhancers, stabilizing agents, gelling agents (such as Carbopol®941, microcrystalline cellulose and carboxymethylcellulose), active agents, humectants, odor absorbers, fragrances, pH-adjusting agents, chelating agents, emulsifiers, occlusive agents, emollients, thickeners, solubilizing agents, penetration enhancers, anti-irritants, colorants, propellants, etc. The choice and amount of the aforesaid additives are within the expertise and the routine skills of those skilled in the art.

The pharmaceutical composition according to the present disclosure may further include one or more of the following pharmaceutically acceptable solvents: water, normal saline, phosphate buffered saline (PBS), sugar-containing solutions, and aqueous solutions containing alcohol.

The dosage and frequency of administration of the pharmaceutical composition according to the present disclosure may vary depending on the following factors: the severity of the disease to be alleviated, the route of administration, and the age, physical condition and response of the subject to be treated. For instance, the dosage and frequency of topical administration of the pharmaceutical composition according to the present disclosure may be 0.01-0.05 mg/cm$^2$ of the skin area, one to three times per day. The dosage and frequency of parenteral or oral administration of the pharmaceutical composition may be 25-50 mg/kg, once per day.

In the present disclosure, the inventors found that pretreatment of cells with isorhamnetin-3-O-β-D-glucoside is able to effectively protect human skin keratinocytes against ultraviolet-induced apoptosis. Therefore, the composition used in the method of the present disclosure may be a cosmetic composition.

According to the present disclosure, the cosmetic composition may further include a cosmetically acceptable adjuvant that is widely employed in cosmetic-manufacturing technology.

The cosmetically acceptable adjuvant may include one or more of the following reagents: solvents, gelling agents, activating agents, preservatives, antioxidants, screening agents, chelating agents, surfactants, coloring agents, thickening agents, fillers, fragrance and odor absorbents. The choice and amount of the aforesaid reagents are within the expertise and the routine skills of those skilled in the art.

The cosmetic composition may be prepared using technology well known to a skilled artisan into the form of, e.g., aqueous solution, aqueous-alcohol solution, oily solution, emulsions (oil-in-water type, water-in-oil type or complex type), gels, ointments, creams, masks, patches, packs, liniments, powder, aerosols, sprays, lotions, serums, pastes, foams, dispersions, drops, or mousse. The cosmetic composition may be used in skincare or makeup products, e.g., sunblock, tonic water, foundation, eyeshadow, makeup remover products, soap, and other body-cleansing products.

The cosmetic composition according to the present disclosure may be used with the following external use agents: whitening agents (such as tretinoin, catechin, kojic acid, arbutin, and vitamin C), humectants, anti-inflammatory agents, bactericides, ultraviolet absorbers, plant extracts (such as aloe extract), skin nutrients, anesthetics, anti-acne agent, antipruritics, analgesics, anti-dermatitis agents, antihyperkeratolytic agents, anti-dry skin agents, anti-psoriatic agents, antiaging agents, anti-wrinkle agents, anti-seborrheic agents, wound-healing agents, corticosteroids, hormones, free radical scavengers (e.g., catalase), antioxidants (e.g., vitamin E), cytokines (e.g., interleukin-1), thiols (e.g., Amifostine), and steroids (e.g., 5-Androstenediol). The choice and amount of the aforesaid external use agents are within the expertise and the routine skills of those skilled in the art.

According to the present disclosure, the cosmetic composition is in a form for topical administration. For instance, the daily dosage and frequency of topical administration of the cosmetic composition according to the present disclosure may be 1-5 μg/cm$^2$ of the skin area, two to five times per day.

The present disclosure will be further described in the following examples. However, it should be understood that the following examples are solely intended for the purpose of illustration and should not be construed as limiting the present disclosure in practice.

EXAMPLES

Experimental Materials

1. Source and Cultivation of Cell Lines

The following cell lines used in the examples were: mouse liver cell line BNL CL.2 (ATCC TIB-73; BCRC 60180) and mouse mammary gland epithelial cell line NMuMG (ATCC CRL-1636; BCRC 60087) purchased from the Bioresource Collection and Research Center of the Food Industry Research and Development Institute (BCRC of FIRDI, Taiwan), and human skin keratinocyte cell line HaCaT provided by Dr. Chih-Yang Huang (Graduate Institute of Basic Medical Science, China Medical University, Taichung City, Taiwan).

Each of the cell lines were cultivated using a corresponding medium shown in Table 1 and a 6-cm Petri dish in an incubator (37° C. and 5% $CO_2$). When about 80-90% confluence was reached, medium was removed, followed by washing the cells once with phosphate buffered saline (PBS) (pH 7.4; Gibco). Trypsin-EDTA was added so as to detach the cells from the bottom of the Petri dish. Subsequently, a fresh medium was added to neutralize the activity of the trypsin, and the cells were sufficiently dispersed by virtue of repeated aspiration with a pipette. The resultant cell suspension was transferred to a flask, followed by cultivation in an incubator.

TABLE 1

| Cell line | Medium |
| --- | --- |
| BNL CL.2 and HaCaT | Dulbecco's Modified Eagle's Medium (DMEM)(Gibco) supplemented with 10% fetal bovine serum (FBS)(Gibco), 100 U/mL penicillin, and 100 mg/mL streptomycin (Gibco) |
| NMuMG | DMEM supplemented with 10% FBS, 100 U/mL penicillin, 100 mg/mL streptomycin, and 10 µg/mL insulin |

2. Preparation of Stock Solutions

The preparation processes of two stock solutions used in the examples are described as follows:

(1) Stock Solution of Isorhamnetin-3-O-β-D-Glucoside

Isorhamnetin-3-O-β-D-glucoside (Shanghai Beizhuo Biotechnology Co., Ltd., Cat. No. 5041-82-7) was dissolved in dimethylsulfoxide (DMSO) so as to obtain a stock solution having a concentration of 10 mM.

(2) Stock Solution of Isorhamnetin

Isorhamnetin (Shanghai Yuanye Bio-Technology Co., Ltd., Cat. No. 480-19-3) was dissolved in DMSO so as to obtain a stock solution having a concentration of 10 mM.

General Experimental Procedure:

Statistical Analysis

In the following examples, each group was subjected to the same experiment three times. The experimental data are expressed as mean±standard error of the mean (SEM), and were analyzed using paired Student's t-test so as to assess the difference between all the groups. $p<0.05$ indicates a statistically significant difference.

Example 1

Effect of Isorhamnetin-3-O-β-D-Glucoside on X-Ray-Induced Death

Experimental Procedures:

A. Treatment of Mouse Liver Cell Line BNL CL.2 and Mouse Mammary Gland Epithelial Cell Line NMuMG Using Isorhamnetin-3-O-β-D-Glucoside Eight groups of BNL CL.2 cells (i.e., a normal control group referred to as Normal Control Group 1-A, an isorhamnetin-3-O-β-D-glucoside group referred to as Isorhamnetin-3-O-β-D-glucoside Group 1-A, three X-ray control groups referred to as X-Ray Control Groups 1-A to 3-A, and three experimental groups referred to as Experimental Groups 1-A to 3-A) and eight groups of NMuMG cells (i.e., a normal control group referred to as Normal Control Group 1-B, an isorhamnetin-3-O-β-D-glucoside group referred to as Isorhamnetin-3-O-β-D-glucoside Group 1-B, three X-ray control groups referred to as X-Ray Control Groups 1-B to 3-B, and three experimental groups referred to as Experimental Groups 1-B to 3-B) were prepared based on the procedure set forth in "Source and cultivation of cell lines" of "Experimental materials". Specifically, BNL CL.2 cells in each group were cultivated using 5 mL of a corresponding medium shown in Table 1 and a 6-cm Petri dish in an amount of $2\times10^5$ cells per dish. Likewise, NMuMG cells in each group were cultivated using 5 mL of a corresponding medium shown in Table 1 and a 6-cm Petri dish in an amount of $2.5\times10^5$ cells per dish. The cultivation was conducted in an incubator (37° C., 5% $CO_2$) for 24 hours.

Subsequently, medium was replaced with fresh medium, and a suitable amount of isorhamnetin-3-O-β-D-glucoside stock solution was added to the obtained culture in each of Isorhamnetin-3-O-β-D-glucoside Group 1-A, Isorhamnetin-3-O-β-D-glucoside Group 1-B, Experimental Groups 1-A to 3-A, and Experimental Groups 1-B to 3-B such that the final concentration of isorhamnetin-3-O-β-D-glucoside in each of the cultures was 30 µM. Isorhamnetin-3-O-β-D-glucoside stock solution was not added to the cultures in Normal Control Group 1-A, Normal Control Group 1-B, X-Ray Control Groups 1-A to 3-A, and X-Ray Control Groups 1-B to 3-B.

The culture in each group was then cultivated in an incubator (37° C., 5% $CO_2$) for two hours. The resultant culture was used for the following clonogenic assay.

B. Clonogenic Assay

The cultures in Experimental Groups 1-A to 3-A, Experimental Groups 1-B to 3-B, X-Ray Control Groups 1-A to 3-A, and X-Ray Control Groups 1-B to 3-B, prepared according to section A of "Experimental procedures" in this example, were subjected to X-ray irradiation (6 MeV) using a linear accelerator at a corresponding dose shown in Table 2. The cultures in Normal Control Group 1-A, Normal Control Group 1-B, Isorhamnetin-3-O-β-D-glucoside Group 1-A, and Isorhamnetin-3-O-β-D-glucoside Group 1-B received no X-ray irradiation treatment.

TABLE 2

| Group | Dose (Gy) |
| --- | --- |
| X-Ray Control Group 1-A | 2 |
| X-Ray Control Group 1-B | 2 |

TABLE 2-continued

| Group | Dose (Gy) |
|---|---|
| X-Ray Control Group 2-A | 4 |
| X-Ray Control Group 2-B | 4 |
| X-Ray Control Group 3-A | 6 |
| X-Ray Control Group 3-B | 6 |
| Experimental Group 1-A | 2 |
| Experimental Group 1-B | 2 |
| Experimental Group 2-A | 4 |
| Experimental Group 2-B | 4 |
| Experimental Group 3-A | 6 |
| Experimental Group 3-B | 6 |

The culture in each group was cultivated in an incubator (37° C., 5% $CO_2$) for two hours. 0.5 mL of trypsin-EDTA was added to the culture in each group so as to detach the cells from the bottom of the Petri dish. Following this, 2 mL of a fresh medium (corresponding to the medium described in Table 1) was added to neutralize the activity of the trypsin, and the cells were sufficiently dispersed by virtue of repeated aspiration with a pipette. The resultant cell suspension was transferred to a new 6-cm Petri dish, in which the plated cell number in each of Isorhamnetin-3-O-β-D-glucoside Group 1-A, Isorhamnetin-3-O-β-D-glucoside Group 1-B, Normal Control Group 1-A, and Normal Control Group 1-B was $2.0 \times 10^2$ cells per dish; the plated cell number in each of Experimental Group 1-A, Experimental Group 1-B, X-Ray Control Group 1-A, and X-Ray Control Group 1-B was $4.0 \times 10^2$ cells per dish; the plated cell number in each of Experimental Group 2-A, Experimental Group 2-B, X-Ray Control Group 2-A, and X-Ray Control Group 2-B was $8.0 \times 10^2$ cells per dish; and the plated cell number in each of Experimental Group 3-A, Experimental Group 3-B, X-Ray Control Group 3-A, and X-Ray Control Group 3-B was $1.6 \times 10^3$ cells per dish.

The cells in each group were cultivated in an incubator (37° C., 5% $CO_2$) for two weeks. The resultant cell colonies in each group were fixed with 5 mL of 4% formaldehyde, after which 5 mL of 0.005% (w/v) crystal violet was added, followed by reaction at 25° C. for 30 minutes. The number of cell colonies was counted using an inverted microscope (Olympus CH40) at 100× magnification.

The plating efficiency (PE)(%) of each group was calculated using the following formula (1):

$$A = (B/C) \times 100 \quad (1)$$

A: plating efficiency (%)
B: the number of cell colonies
C: the plated cell number The survival fraction of each of Isorhamnetin-3-O-β-D-glucoside Group 1-A and Experimental Groups 1-A to 3-A was calculated by dividing the plating efficiency of the group by the plating efficiency of Isorhamnetin-3-O-β-D-glucoside Group 1-A Likewise, the survival fraction of each of Isorhamnetin-3-O-β-D-glucoside Group 1-B and Experimental Groups 1-B to 3-B was calculated by dividing the plating efficiency of the group by the plating efficiency of Isorhamnetin-3-O-β-D-glucoside Group 1-B. In addition, the survival fraction of each of Normal Control Group 1-A and X-Ray Control Groups 1-A to 3-A was calculated by dividing the plating efficiency of the group by the plating efficiency of Normal Control Group 1-A. Similarly, the survival fraction of each of Normal Control Group 1-B and X-Ray Control Groups 1-B to 3-B was calculated by dividing the plating efficiency of the group by the plating efficiency of Normal Control Group 1-B. The data thus obtained were analyzed according to the method described in the "Statistical analysis" section of "General experimental procedure".

Figure 2:
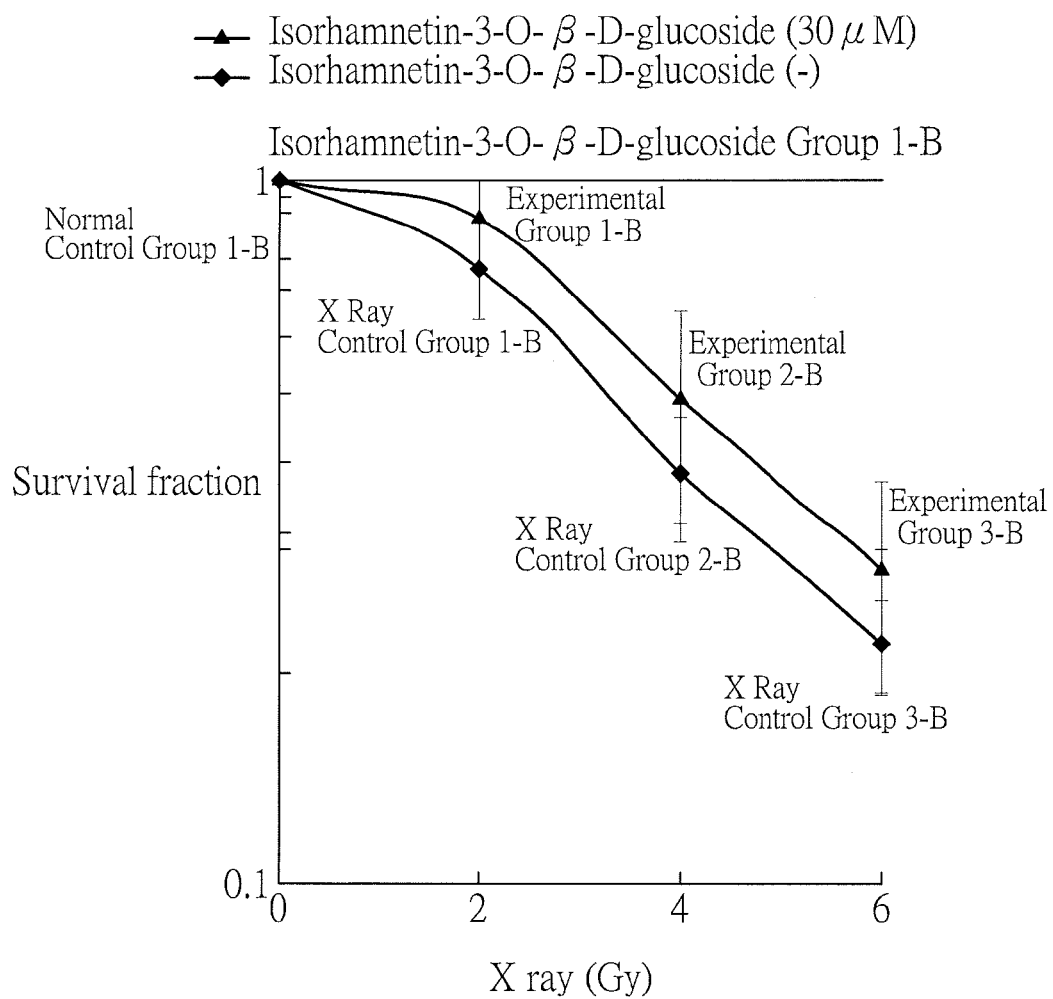
FIG. 2 shows the survival fraction of NMuMG cells in each group as determined via clonogenic assay.

Results:

FIGS. 1 and 2 respectively show the survival fractions of the groups in BNL CL.2 and NMuMG cell lines as determined via clonogenic assay. Regardless of the cell line, x-ray control groups exhibit a significant reduction in survival fraction as compared to the normal control group. Similarly, experimental groups exhibit a significant reduction in survival fraction as compared to Isorhamnetin-3-O-β-D-glucoside groups. Such reduction becomes more apparent as the dose of X-ray irradiation increases, thereby indicating that X-rays inhibit the growth of BNL CL.2 and NMuMG cells. Moreover, in BNL CL.2 cells, the survival fraction of the experimental group was higher than that of the X-ray control group at each X-ray irradiation dose. Similarly, in NMuMG cells, the survival fraction of the experimental group was higher than that of the X-ray control group at each X-ray irradiation dose. The aforesaid results show that isorhamnetin-3-O-β-D-glucoside is able to protect cells against X-ray-induced death.

Example 2

Effect of Isorhamnetin-3-O-β-D-Glucoside on X Ray-Induced Cell Death

Experimental Procedures:

A. Treatment of Mouse Mammary Gland Epithelial Cell Line NMuMG Using Isorhamnetin-3-O-β-D-Glucoside Four groups of NMuMG cells (i.e., a normal control group, an X-ray control group, and two experimental groups referred to as Experimental Groups 1 to 2) were prepared based on the procedure set forth in "Source and cultivation of cell lines" of "Experimental materials". NMuMG cells in each group were cultivated using 5 mL of a corresponding medium shown in Table 1 and a 6-cm Petri dish in an amount of $2.5 \times 10^5$ cells per dish. The cultivation was conducted in an incubator (37° C., 5% $CO_2$) for 24 hours.

Subsequently, medium was replaced with fresh medium, and a suitable amount of isorhamnetin-3-O-β-D-glucoside stock solution was added to the obtained culture in each of Experimental Groups 1 and 2, such that the final concentration of isorhamnetin-3-O-β-D-glucoside in the culture in Experimental Group 1 was 15 μM, and the final concentration of isorhamnetin-3-O-β-D-glucoside in the culture in Experimental Group 2 was 30 μM. Isorhamnetin-3-O-β-D-glucoside stock solution was not added to the cultures in the normal control group and the X-ray control group.

The culture in each group was then cultivated in an incubator (37° C., 5% $CO_2$) for two hours. The resultant culture was used for the following cell cycle analysis.

B. Cell Cycle Analysis

The cultures in the X-ray control group and Experimental Groups 1 to 2, prepared according to section A of "Experimental procedures" in this example, were subjected to X-ray irradiation using a linear accelerator at a dose of 20 Gy. The culture in the normal control group received no X-ray irradiation treatment. The culture in each group was cultivated in an incubator (37° C., 5% $CO_2$) for 96 hours, followed by centrifugation at 25° C. and 1200 rpm for 3 minutes. The supernatant was removed, and the precipitate thus obtained was washed with cold PBS (pH 7.4), followed by fixing the cells with 1 mL of cold methanol. The fixed cells thus obtained were left standing at −20° C. overnight. Following this, the fixed cells were washed with cold PBS (pH 7.4), and 250 μL of cold DNA dying solution which was prepared in ddH$_2$O, containing 200 µg/mL RNase A solution (Sigma-Aldrich), 50 µg/mL propidium iodide (PI)(Sigma-Aldrich), and 0.1% (v/v) Triton X-100, was added to re-suspend the cells in each group. The cells were kept in the dark for 30 minutes at 37° C. to obtain stained cells.

Subsequently, the stained cells thus obtained were subjected to cell cycle analysis using BD Accuri™ C6 flow cytometer (BD Biosciences), and 1.0×10$^6$ cells were analyzed in each analysis. The cells emitted fluorescence when excited by a laser beam of argon ion at 488 nm, and the fluorescence intensity was detected at a wavelength of 585 nm. The percentage of the cells in each cell cycle phase was analyzed using BD Accuri™ C6 software (BD Biosciences).

Afterward, the data thus obtained were analyzed according to the method described in the "Statistical analysis" section of "General experimental procedure".

Results:

The cell cycle distribution of NMuMG cells in each group is shown in Table 3. As shown in Table 3, the cell percentage in Sub-G1 phase in the X-ray control group is higher than that of the normal control group, thereby indicating that X-rays can induce apoptosis in NMuMG cells. In addition, the cell percentage in Sub-G1 phase in Experimental Groups 1 and 2 is lower than that of the X-ray control group, and such lower percentage becomes more apparent as the concentration of isorhamnetin-3-O-β-D-glucoside increases. The aforesaid results show that isorhamnetin-3-O-β-D-glucoside is able to protect cells against X-ray-induced cell death.

TABLE 3

| Group | The percentage of the cells in each cell cycle phase (%) | | | |
| --- | --- | --- | --- | --- |
| | Sub-G1 | G0/G1 | S | G2/M |
| Normal control group | 0.53 ± 0.12 | 36.73 ± 13.77 | 1.83 ± 0.33 | 61.17 ± 14.04 |
| X-ray control group | 20.23 ± 1.28** | 17.2 ± 5.19* | 5.6 ± 1.93 | 57.67 ± 5.07 |
| Experimental Group 1 | 16.11 ± 2.03## | 21 ± 4.31# | 6.4 ± 0.28 | 58.76 ± 8.97 |
| Experimental Group 2 | 13.88 ± 1.46## | 22.25 ± 4.87# | 5.88 ± 1.2 | 59.63 ± 10.78 |

*$p < 0.05$ when compared to the normal control group.
**$p < 0.01$ when compared to the normal control group.
$p < 0.05$ when compared to the X-ray control group.
$p < 0.01$ when compared to the X-ray control group.

Example 3

Effect of Isorhamnetin-3-O-β-D-Glucoside on X Ray-Induced Apoptosis

In this example, the inventors pretreated cells with either isorhamnetin-3-O-β-D-glucoside or isorhamnetin to investigate the effect of such pretreatment on X-ray-induced apoptosis.

Experimental Procedures:

A. Pretreatment of Mouse Liver Cell Line BNL CL.2 and Mouse Mammary Gland Epithelial Cell Line NMuMG Four groups of BNL CL.2 cells (i.e., a normal control group referred to as Normal Control Group 1-A, an X-ray control group referred to as X-Ray Control Group 1-A, and two experimental groups referred to as Experimental Groups 1-A to 2-A), and six groups of NMuMG cells (i.e., a normal control group referred to as Normal Control Group 1-B, an X-ray control group referred to as X-Ray Control Group 1-B, two isorhamnetin groups referred to as Isorhamnetin Groups 1 to 2, and two experimental groups referred to as Experimental Groups 1-B to 2-B), were prepared based on the procedure set forth in "Source and cultivation of cell lines" of "Experimental materials". BNL CL.2 cells in each group were cultivated using 5 mL of a corresponding medium shown in Table 1 and a 6-cm Petri dish in an amount of 2×10$^5$ cells per dish. Likewise, NMuMG cells in each group were cultivated using 5 mL of a corresponding medium shown in Table 1 and a 6-cm Petri dish in an amount of 2.5×10$^5$ cells per dish. The cultivation was conducted in an incubator (37° C., 5% CO$_2$) for 24 hours.

Subsequently, medium was replaced with fresh medium. The obtained cultures in Experimental Groups 1-A, 1-B, 2-A, and 2-B were pretreated with the stock solution of isorhamnetin-3-O-β-D-glucoside, and the obtained cultures in Isorhamnetin Groups 1 to 2 were pretreated with the stock solution of isorhamnetin. The pretreated condition of the culture in each group is shown in Table 4.

TABLE 4

| | | Pretreated condition | |
| --- | --- | --- | --- |
| Cell line | Group | Isorhamnetin (µM) | Isorhamnetin-3-O-β-D-glucoside (µM) |
| BNL CL.2 | Normal Control Group 1-A | — | — |
| | X-Ray Control Group 1-A | — | — |
| | Experimental Group 1-A | — | 5 |
| | Experimental Group 2-A | — | 30 |
| NMuMG | Normal Control Group 1-B | — | — |
| | X-Ray Control Group 1-B | — | — |
| | Isorhamnetin Group 1 | 15 | — |
| | Isorhamnetin Group 2 | 30 | — |
| | Experimental Group 1-B | — | 15 |

TABLE 4-continued

| | | Pretreated condition | |
|---|---|---|---|
| Cell line | Group | Isorhamnetin (μM) | Isorhamnetin-3-O-β-D-glucoside (μM) |
| | Experimental Group 2-B | — | 30 |

The culture in each group was then cultivated in an incubator (37° C., 5% $CO_2$) for two hours. The resultant culture was used for the following experiments in sections B to D.

B. Apoptosis Assay

The cultures in X-Ray Control Group 1-A, X-Ray Control Group 1-B, Isorhamnetin Group 1, Isorhamnetin Group 2, Experimental Group 1-A, Experimental Group 1-B, Experimental Group 2-A, and Experimental Group 2-B, prepared according to section A of "Experimental procedures" in this example, were subjected to X-ray irradiation using a linear accelerator at a dose of 15 Gy. The cultures in Normal Control Groups 1-A and 1-B received no X-ray irradiation treatment. The culture of BNL CL.2 cells in each group was cultivated using a 6-cm Petri dish in an incubator (37° C., 5% $CO_2$) for 96 hours, and the culture of NMuMG cells in each group was cultivated using a 6-cm Petri dish in an incubator (37° C., 5% $CO_2$) for 72 hours. 1 mL of trypsin-EDTA was added to the culture in each group so as to detach the cells from the bottom of the Petri dish. Following this, 1 mL of a fresh medium (corresponding to the medium described in Table 1) was added to neutralize the activity of the trypsin, and the resultant cell suspension was transferred to a centrifuge tube with a pipette, followed by centrifugation at 1200 rpm for three minutes. The supernatant was removed, and the cell pellet thus obtained was washed once with cold PBS (pH 7.4), followed by centrifugation at 1200 rpm for 3 minutes. The supernatant was removed, and 100 μL of cold Annexin V binding buffer (BD Pharmingen™) was added to sufficiently re-suspend the cell pellet thereby obtaining a cell suspension having a cell concentration of $1.0 \times 10^6$ cells/mL. Afterward, 5 μL of FITC Annexin V (BD Pharmingen™) and 5 μL of propidium iodide (PI) staining solution (BD Pharmingen™) were added to the obtained cell suspension, followed by mixing evenly and standing in the dark at 4° C. for 30 minutes so as to obtain stained cells.

Subsequently, the stained cells were analyzed using BD Accuri™ C6 flow cytometry, in which cells that could be stained with FITC Annexin V but not with PI (i.e., FITC Annexin V positive and PI negative) represented cells that were induced with early apoptosis; cells stained with both FITC Annexin V and PI (i.e., FITC Annexin V positive and PI positive) represented cells that were induced with late apoptosis; and cells that could not be stained with FITC Annexin V and PI (i.e., FITC Annexin V negative and PI negative) represented viable cells. The number of stained cells was calculated using BD Accuri™ C6 software.

The apoptosis percentage (%) of each group was calculated using the following formula (2):

$$D = [(E+F)/G] \times 100 \quad (2)$$

D: apoptosis percentage (%)
E: the number of cells that was stained with FITC Annexin V but not with PI
F: the number of cells stained with FITC Annexin V and PI
G: the number of total cells Afterward, the data thus obtained were analyzed according to the method described in the "Statistical analysis" section of "General experimental procedure".

C. Mitochondrial Membrane Potential Assay

It is known that depolarization of the mitochondrial membrane potential is an early marker of apoptosis. Consequently, in order to examine whether isorhamnetin-3-O-β-D-glucoside has an effect on the mitochondrial membrane potential of BNL CL.2 cells and NMuMG cells in protecting these cell lines against X-ray-induced apoptosis, the following experiments were conducted.

The cultures in X-Ray Control Group 1-A and Experimental Group 1-A, prepared according to section A of "Experimental procedures" in this example, were subjected to X-ray irradiation using a linear accelerator at a dose of 15 Gy. The cultures in X-Ray Control Group 1-B and Experimental Group 1-B, prepared according to section A of "Experimental procedures" in this example, were subjected to X-ray irradiation using the linear accelerator at a dose of 10 Gy. The cultures in Normal Control Groups 1-A and 1-B received no X-ray irradiation treatment.

Subsequently, BNL CL.2 cells in each group was cultivated using a 6-cm Petri dish in an incubator (37° C., 5% $CO_2$) for 120 hours, and NMuMG cells in each group was cultivated using a 6-cm Petri dish in an incubator (37° C., 5% $CO_2$) for 48 hours, followed by washing the resultant cell culture in each group once with PBS. 1 mL of trypsin-EDTA was added so as to detach the cells from the bottom of the Petri dish. Afterward, 1 mL of a fresh medium (corresponding to the medium described in Table 1) was added to neutralize the activity of the trypsin, and the resultant cell suspension was transferred to a centrifuge tube with a pipette, followed by centrifugation at 400×g for 5 minutes. The supernatant was removed, and 500 μL of 1×JC-1 staining buffer was added, followed by standing in the dark at 37° C. for 15 minutes so as to obtain stained cells. 1 mL of JC-1 assay buffer was added to wash the stained cells, followed by centrifugation at 400×g for 5 minutes. The supernatant was removed, and 500 μL of JC-1 assay buffer was added to re-suspend the cells. Mitochondrial membrane potential assay was conducted using BD Accuri™ C6 flow cytometry, and the percentage of mitochondrial membrane potential depolarization (%) was calculated using BD Accuri™ C6 software.

Afterward, the data thus obtained were analyzed according to the method described in the "Statistical analysis" section of "General experimental procedure".

D. Expression Profile of Cleaved Caspase-9

The cultures in X-Ray Control Group 1-A, X-Ray Control Group 1-B, Experimental Group 1-A, Experimental Group 1-B, Experimental Group 2-A, and Experimental Group 2-B, prepared according to section A of "Experimental procedures" in this example, were subjected to X-ray irradiation using a linear accelerator at a dose of 15 Gy. The cultures in Normal Control Groups 1-A and 1-B received no X-ray irradiation treatment.

Subsequently, the culture in each group was cultivated in an incubator (37° C., 5% $CO_2$) for 48 hours, and 120 μL of lysis buffer containing CelLytic™ M protein extraction reagent (Sigma-Aldrich) and proteinase inhibitor cocktail (Sigma-Aldrich) was added to the culture in each group, followed by mixing evenly. The resultant cell mixture was placed in a microcentrifuge tube, and centrifugation was conducted at 4° C. and 13000 rpm for 10 minutes, followed by collection of the supernatant to serve as a total protein sample. Protein concentration in the total protein sample was determined by means of the Bio-Rad Protein Assay Kit.

The total protein sample in each group was subjected to sodium dodecyl sulfate-polyacrylamide gel electrophoresis (SDS-PAGE) analysis and Western Blotting analysis according to the technique well known to and routinely used by one skilled in the art, in which the total protein sample was subjected to Western Blotting analysis of cleaved caspase-9. In addition, β-actin was used as an internal control.

The instruments and reagents used for SDS-PAGE analysis and Western Blotting analysis are as follows:
(1) SDS-PAGE analysis was performed using an electrophoresis system (Bio-Rad)
(2) Protein transfer was performed using a semi-dry electrophoretic transfer cell (Bio-Rad) and a polyvinylidene difluoride (PVDF) membrane.
(3) In Western Blotting analysis, primary and secondary antibodies used for detecting each protein are shown in Table 5.

TABLE 5

| Protein | Primary antibody | Secondary antibody |
|---|---|---|
| Cleaved caspase-9 | Mouse anti cleaved caspase-9 monoclonal antibody (BD Biosciences, Cat. No. 551246) | Goat anti mouse IgG-horseradish peroxidase (HRP) antibody (Millipore, Cat. No. AP124P) |
| β-actin | Mouse anti β-actin monoclonal antibody (Sigma-Aldrich, Cat. No. A5441) | Goat anti mouse IgG-HRP antibody (Millipore, Cat. No. AP124P) |

(4) Chemiluminescence staining was performed using chemiluminescent HRP substrate (Millipore, Cat. No. WBKLS0500), and signal detection was performed using ImageScanner Imaging Software (GE Healthcare Life Sciences).

Subsequently, ImageScanner Imaging Software was used for analysis, such that the corresponding protein expression level was semi-quantitatively calculated. The expression level of cleaved caspase-9 in each group was normalized by the expression level of corresponding β-actin thereof. The normalized expression level of cleaved caspase-9 in each of Normal Control Group 1-A and Normal Control Group 1-B was regarded as 100%. The percentage of the expression level of cleaved caspase-9 associated with BNL CL.2 cells in each of the other groups relative to the expression level of cleaved caspase-9 in Normal Control Group 1-A was calculated, and the percentage of the expression level of cleaved caspase-9 associated with NMuMG cells in each of the other groups relative to the expression level of cleaved caspase-9 in Normal Control Group 1-B was calculated. Afterward, the data thus obtained were analyzed according to the method described in the "Statistical analysis" section of "General experimental procedure".

Results:

A. Apoptosis Assay

The apoptosis percentages of groups in BNL CL.2 and NMuMG cell lines as determined via apoptosis assay are shown in Table 6. As shown in Table 6, regardless of the cell line, the X-ray control group exhibits a significant increase in apoptosis percentage as compared to the normal control group, thereby indicating that X-rays can induce apoptosis in BNL CL.2 cells and NMuMG cells. In addition, Experimental Groups 1-A and 2-A exhibit a significant reduction in apoptosis percentage as compared to X-Ray Control Group 1-A Likewise, Experimental Groups 1-B and 2-B exhibit a significant reduction in apoptosis percentage as compared to X-Ray Control Group 1-B. Such reduction becomes more apparent as the concentration of isorhamnetin-3-O-β-D-glucoside increases. Considering NMuMG cells, the apoptosis percentages of Experimental Groups 1-B and 2-B are significantly lower than those of Isorhamnetin Groups 1 and 2. The aforesaid results show that isorhamnetin-3-O-β-D-glucoside is more effective in protecting cells against X-ray-induced apoptosis as compared to isorhamnetin.

TABLE 6

| Cell line | Group | Apoptosis percentage (%) |
|---|---|---|
| BNL CL.2 | Normal Control Group 1-A | 3.63 ± 1.11 |
| | X-Ray Control Group 1-A | 32.28 ± 1.3** |
| | Experimental Group 1-A | 30.28 ± 3.09 |
| | Experimental Group 2-A | 29.35 ± 1.92# |
| NMuMG | Normal Control Group 1-B | 2.23 ± 0.21 |
| | X-Ray Control Group 1-B | 23.23 ± 1.22** |
| | Isorhamnetin Group 1 | 22.87 ± 1.33 |
| | Isorhamnetin Group 2 | 22.13 ± 0.29 |
| | Experimental Group 1-B | 17.77 ± 0.88## |
| | Experimental Group 2-B | 16.5 ± 0.62## |

**$p < 0.01$ when compared to the normal control group.
$p < 0.05$ when compared to the X-ray control group.
$p < 0.01$ when compared to the X-ray control group.

B. Mitochondrial Membrane Potential Assay

The percentage of mitochondrial membrane potential depolarization of groups in BNL CL.2 and NMuMG cell lines as determined via mitochondrial membrane potential assay is shown in Table 7. As shown in Table 7, regardless of the cell line, the X-ray control group exhibits a significant increase in percentage of mitochondrial membrane potential depolarization as compared to the normal control group, thereby indicating that X-rays can induce apoptosis in BNL CL.2 cells and NMuMG cells. In addition, Experimental Group 1-A exhibits a significant reduction in percentage of mitochondrial membrane potential depolarization as compared to X-Ray Control Group 1-A. Similarly, Experimental Group 1-B exhibits a significant reduction in percentage of mitochondrial membrane potential depolarization as compared to X-Ray Control Group 1-B. The aforesaid results show that isorhamnetin-3-O-β-D-glucoside is able to inhibit mitochondrial membrane potential depolarization after X-ray irradiation, thereby achieving protection of cells against X-ray-induced apoptosis.

TABLE 7

| Cell line | Group | Percentage of mitochondrial membrane potential depolarization (%) |
|---|---|---|
| BNL CL.2 | Normal Control Group 1-A | 7.3 ± 1.49 |
| | X-Ray Control Group 1-A | 20.33 ± 3.53* |
| | Experimental Group 1-A | 16 ± 2.97# |
| NMuMG | Normal Control Group 1-B | 11.28 ± 2.77 |
| | X-Ray Control Group 1-B | 33.25 ± 1.93** |
| | Experimental Group 1-B | 30.05 ± 1.07# |

*$p < 0.05$ when compared to the normal control group.
**$p < 0.01$ when compared to the normal control group.
$p < 0.05$ when compared to the X-ray control group.

C. Expression Profile of Cleaved Caspase-9

Figure 3:
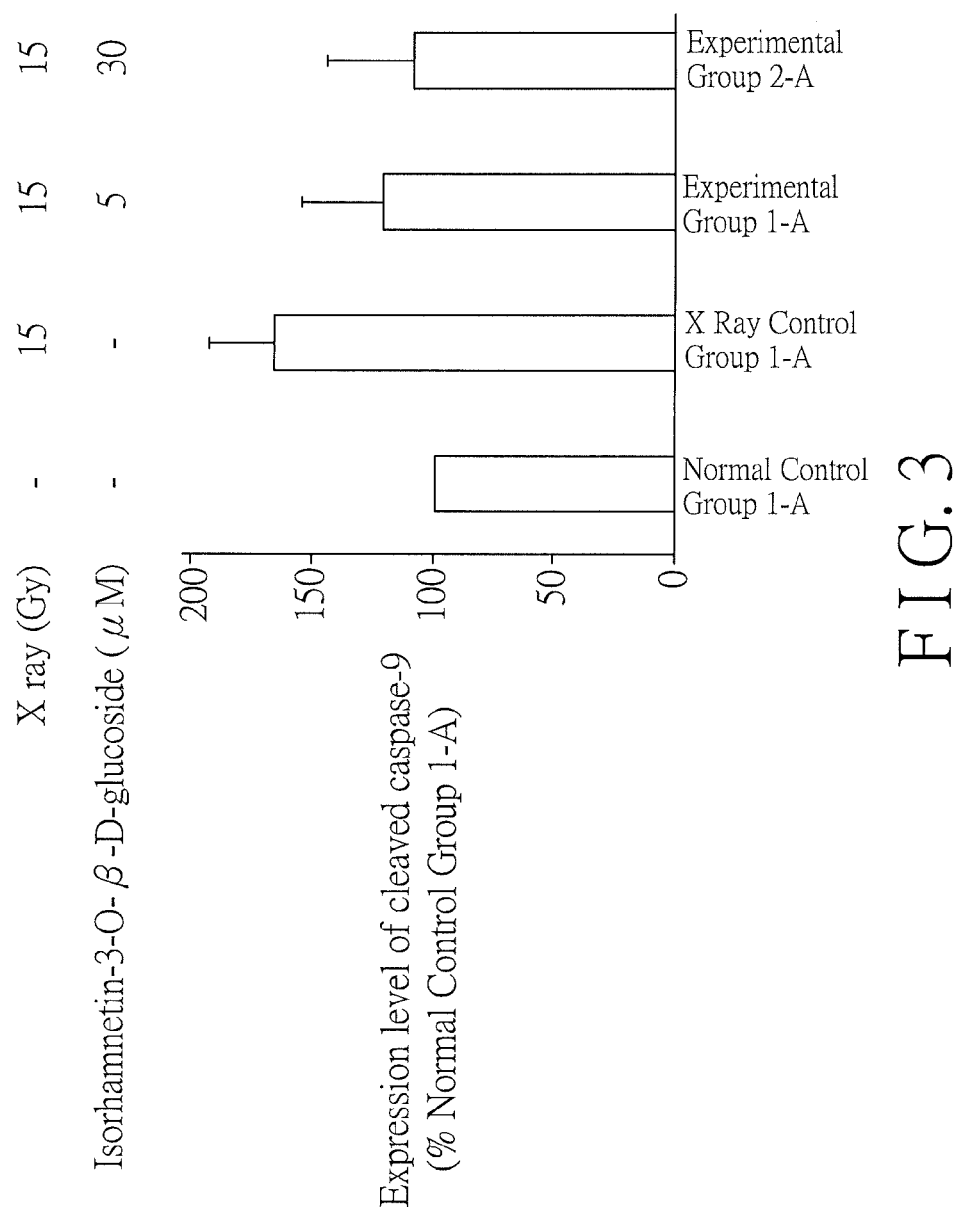
FIG. 3 shows the expression profile of cleaved caspase-9 in BNL CL.2 cells in each group as determined via Western Blotting analysis.
Figure 4:
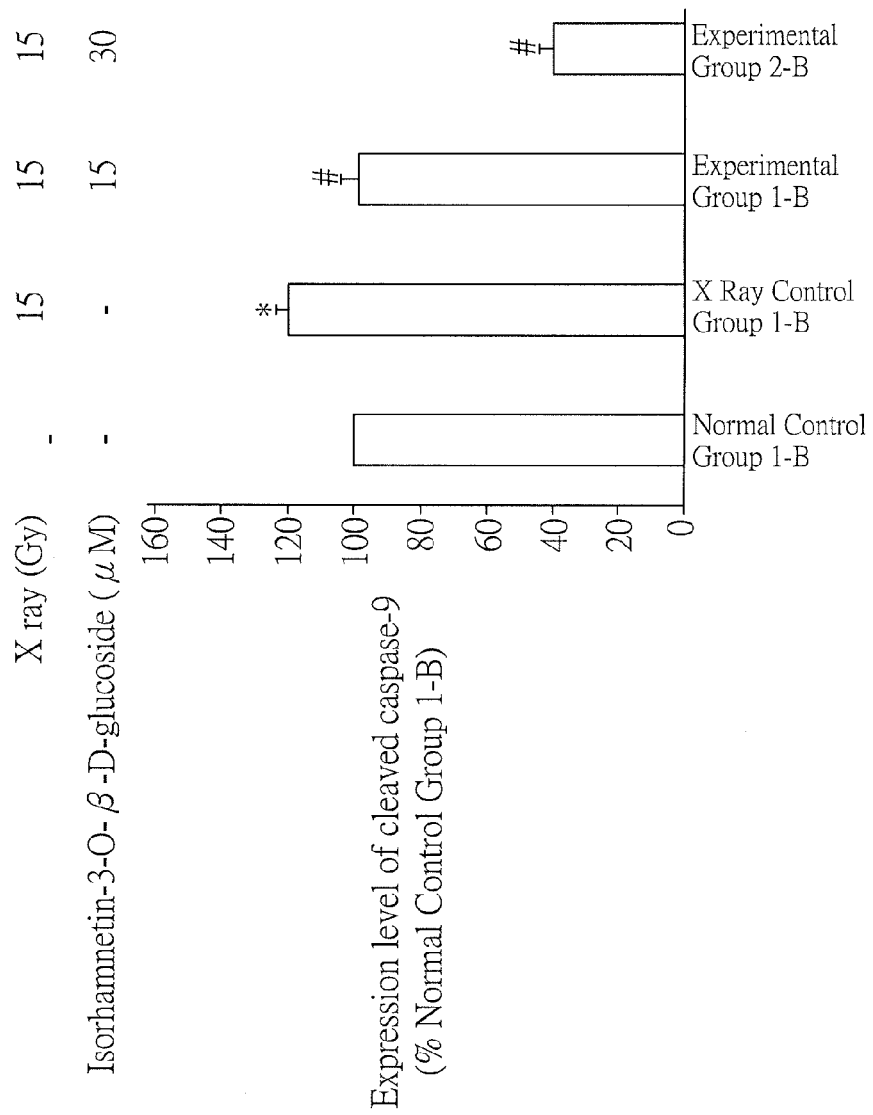
FIG. 4 shows the expression profile of cleaved caspase-9 in NMuMG cells in each group as determined via Western Blotting analysis, in which the symbol "*" represents p<0.05 when compared with Normal Control Group 1-B; and the symbol "#" represents p<0.05 when compared with X-Ray Control Group 1-B.

FIGS. 3 and 4 respectively show the expression profiles of cleaved caspase-9 in BNL CL.2 and NMuMG cells in each group as determined via Western Blotting analysis. Regardless of the cell line, the X-ray control group exhibits a significant increase in the expression level of cleaved caspase-9 as compared to the normal control group (the expression level of cleaved caspase-9 in the normal control group was regarded as 100%), thereby indicating that X-rays can induce apoptosis in BNL CL.2 and NMuMG cells. In addition, Experimental Groups 1-A and 2-A exhibit a significant reduction in expression level of cleaved caspase-9 as compared to X-Ray Control Group 1-A. Similarly, Experimental Groups 1-B and 2-B exhibit a significant reduction in expression level of cleaved caspase-9 as compared to X-Ray Control Group 1-B. Such reduction becomes more apparent as the concentration of isorhamnetin-3-O-β-D-glucoside increases, especially in NMuMG cells. The aforesaid results show that isorhamnetin-3-O-β-D-glucoside is able to inhibit overexpression of cleaved caspase-9 caused by X-ray irradiation, thereby achieving protection of cells against X-ray-induced apoptosis.

Example 4

Effect of Isorhamnetin-3-O-β-D-Glucoside on Ultraviolet-Induced Apoptosis

Experimental Procedures:
A. Treatment of Mouse Mammary Gland Epithelial Cell Line NMuMG and Human Skin Keratinocyte Cell Line HaCaT Using Isorhamnetin-3-O-β-D-Glucoside Four groups of NMuMG cells (i.e., a normal control group referred to as Normal Control Group 1-A, an ultraviolet control group referred to as UV Control Group 1-A, and two experimental groups referred to as Experimental Groups 1-A to 2-A) and four groups of HaCaT cells (i.e., a normal control group referred to as Normal Control Group 1-B, an ultraviolet control group referred to as UV Control Group 1-B, and two experimental groups referred to as Experimental Groups 1-B to 2-B), were prepared based on the procedure set forth in "Source and cultivation of cell lines" of "Experimental materials". The cells in each group were cultivated using 5 mL of a corresponding medium shown in Table 1 and a 6-cm Petri dish in an incubator (37° C., 5% $CO_2$) for 24 hours.

Subsequently, medium was replaced with fresh medium, and a suitable amount of isorhamnetin-3-O-β-D-glucoside stock solution was added to the obtained culture in each of Experimental Group 1-A, Experimental Group 1-B, Experimental Group 2-A, and Experimental Group 2-B. Isorhamnetin-3-O-β-D-glucoside stock solution was not added to the cultures in Normal Control Group 1-A, Normal Control Group 1-B, UV Control Group 1-A, and UV Control Group 1-B. The final concentration of isorhamnetin-3-O-β-D-glucoside in the culture in each of Experimental Group 1-A, Experimental Group 1-B, Experimental Group 2-A, and Experimental Group 2-B is shown in Table 8.

TABLE 8

| Cell line | Group | Final concentration of isorhamnetin-3-O-β-D-glucoside (μM) |
|---|---|---|
| NMuMG | Experimental Group 1-A | 15 |
|  | Experimental Group 2-A | 30 |
| HaCaT | Experimental Group 1-B | 50 |
|  | Experimental Group 2-B | 100 |

The culture in each group was then cultivated in an incubator (37° C., 5% $CO_2$) for two hours. The resultant culture was used for the following apoptosis assay.

B. Apoptosis Assay

The cultures in UV Control Group 1-A, Experimental Group 1-A, and Experimental Group 2-A, prepared according to section A of "Experimental procedures" in this example, were subjected to ultraviolet irradiation using a CL-1000 ultraviolet crosslinker (UVP) at a dose of 30 mJ/cm². The cultures in UV Control Group 1-B, Experimental Group 1-B, and Experimental Group 2-B, prepared according to section A of "Experimental procedures" in this example, were subjected to ultraviolet irradiation using the CL-1000 ultraviolet crosslinker at a dose of 50 mJ/cm². The culture in Normal Control Groups 1-A and 1-B received no ultraviolet irradiation treatment.

Subsequently, NMuMG cells in each group was cultivated in an incubator (37° C., 5% $CO_2$) for 24 hours, and the culture of HaCaT cells in each group was cultivated in an incubator (37° C., 5% $CO_2$) for 48 hours. 1 mL of trypsin-EDTA was added to the culture in each group so as to detach the cells from the bottom of the Petri dish. Following this, 1 mL of a fresh medium (corresponding to the medium described in Table 1) was added to neutralize the activity of the trypsin, and the resultant cell suspension was transferred to a centrifuge tube with a pipette, followed by centrifugation at 1200 rpm for 3 minutes. The supernatant was removed, and the cell pellet thus obtained was washed once with cold PBS (pH 7.4), followed by centrifugation at 1200 rpm for 3 minutes. The supernatant was removed, and 100 μL of cold Annexin V binding buffer was added to sufficiently re-suspend the cell pellet thereby obtaining a cell suspension having a cell concentration of $1.0 \times 10^6$ cells/mL. Afterward, 5 μL of FITC Annexin V and 5 μL of PI staining solution were added to the obtained cell suspension, followed by mixing evenly and standing in the dark at 4° C. for 30 minutes so as to obtain stained cells.

Subsequently, the stained cells were analyzed using BD Accuri™ C6 flow cytometry, in which cells that could be stained with FITC Annexin V but not with PI (i.e., FITC Annexin V positive and PI negative) represented cells that were induced with early apoptosis; cells stained with both FITC Annexin V and PI (i.e., FITC Annexin V positive and PI positive) represented cells that were induced with late apoptosis; and cells that could not be stained with FITC Annexin V and PI (i.e., FITC Annexin V negative and PI negative) represented viable cells. The number of cells stained with FITC Annexin V and PI was calculated using BD Accuri™ C6 software.

The apoptosis percentage (%) of each group was calculated using the above formula (2). Afterward, the data thus obtained were analyzed according to the method described in the "Statistical analysis" section of "General experimental procedure".

Results:

The apoptosis percentages of groups in NMuMG and HaCaT cell lines as determined via apoptosis assay is shown in Table 9. As shown in Table 9, regardless of the cell line, the apoptosis percentage of the ultraviolet control group is significantly increased as compared to the apoptosis percentage of the normal control group, thereby indicating that ultraviolet can induce apoptosis in NMuMG cells and HaCaT cells. In addition, Experimental Groups 1-A and 2-A exhibit a significant reduction in apoptosis percentage as compared to UV Control Group 1-A Likewise, Experimental Groups 1-B and 2-B exhibit a significant reduction in apoptosis percentage as compared to UV Control Group 1-B. Such reduction becomes more apparent as the concentration of isorhamnetin-3-O-β-D-glucoside increases. The aforesaid results show that isorhamnetin-3-O-β-D-glucoside is able to effectively protect cells against ultraviolet-induced apoptosis.

TABLE 9

| Cell line | Group | Apoptosis percentage (%) |
|---|---|---|
| NMuMG | Normal Control Group 1-A | 5.3 ± 2.9 |
| | UV Control Group 1-A | 17.8 ± 5.1* |
| | Experimental Group 1-A | 10.6 ± 2.8 |
| | Experimental Group 2-A | 10.5 ± 2.5# |
| HaCaT | Normal Control Group 1-B | 2.37 ± 0.44 |
| | UV Control Group 1-B | 45.77 ± 6.38* |
| | Experimental Group 1-B | 26.13 ± 7.26# |
| | Experimental Group 2-B | 23 ± 2.19# |

*$p < 0.05$ when compared to the normal control group.
$p < 0.05$ when compared to the ultraviolet control group.

In view of the foregoing, the inventors opine that isorhamnetin-3-O-β-D-glucoside is useful for the alleviation of radiation injury (including ionizing radiation injury and non-ionizing radiation injury).

All patents and literature references cited in the present specification as well as the references described therein, are hereby incorporated by reference in their entirety. In case of conflict, the present description, including definitions, will prevail.

While the present disclosure has been described with reference to the above specific embodiments, it is apparent that numerous modifications and variations can be made without departing from the scope and spirit of the present disclosure. It is therefore intended that the present disclosure be limited only as indicated by the appended claims.

The invention claimed is:

1. A method for alleviating radiation injury, comprising administering to a subject in need thereof a composition containing isorhamnetin-3-O-β-D-glucoside.

2. The method of claim 1, wherein the radiation injury is an ionizing radiation injury.

3. The method of claim 2, wherein the ionizing radiation injury includes one of an acute radiation syndrome, a chronic radiation syndrome, or injury caused by radiation therapy.

4. The method of claim 1, wherein the radiation injury is a non-ionizing radiation injury.

5. The method of claim 4, wherein the non-ionizing radiation injury is ultraviolet damage.

6. The method of claim 1, wherein the composition is a pharmaceutical composition.

7. The method of claim 6, wherein the pharmaceutical composition further includes a pharmaceutically acceptable carrier.

8. The method of claim 6, wherein the pharmaceutical composition is in a dosage form for parenteral administration.

9. The method of claim 6, wherein the pharmaceutical composition is in a dosage form for oral administration.

10. The method of claim 6, wherein the pharmaceutical composition is in a dosage form for topical administration.

11. The method of claim 1, wherein the composition is a cosmetic composition.

12. The method of claim 11, wherein the cosmetic composition further includes a cosmetically acceptable adjuvant.

13. The method of claim 11, wherein the cosmetic composition is in a form for topical administration.

* * * * *